United States Patent [19]

Mahjour et al.

[11] Patent Number: 4,666,926

[45] Date of Patent: May 19, 1987

[54] TRANSDERMAL FORMULATIONS

[75] Inventors: Majid Mahjour, Morris Plains; Russell U. Nesbitt, Jr., Somerville; Mahdi B. Fawzi, Flanders; Bernadette Tedeschi, Lyndhurst, all of N.J.

[73] Assignee: Warner-Lambert Company, Morris Plains, N.J.

[21] Appl. No.: 833,926

[22] Filed: Feb. 27, 1986

[51] Int. Cl.$^4$ ............................................. A61K 31/44
[52] U.S. Cl. ..................................................... 514/345
[58] Field of Search ......................................... 514/345

[56] References Cited

U.S. PATENT DOCUMENTS

| 4,067,983 | 1/1978 | Poschel et al. | 260/297 R |
| 4,128,555 | 12/1978 | Butler | 546/290 |
| 4,434,169 | 2/1984 | Poschel et al. | 514/345 |

Primary Examiner—Stanley J. Friedman
Attorney, Agent, or Firm—Ronald A. Daignault

[57] ABSTRACT 3-phenoxypyridine and its salts are useful in transdermal formulations as cognition activators.

8 Claims, No Drawings

TRANSDERMAL FORMULATIONS

BACKGROUND

The use of 3-phenoxypyridine and its acid addition salts in oral formulations is disclosed in U.S. Pat. No. 4,434,169. While these oral formulations are effective in treating hippocampal dysfunction, they are nonetheless oral formulations. As such, their use may involve many of the undesirable side effects often associated with oral dosage forms, eg., gastro-intestinal problems, difficulty in swallowing, and the like.

Since many sufferers of psychological disorders are of mature age, they are particularly susceptible to one or more of these side effects. A drug delivery system which obviates the use of oral preparations is highly desirable.

THE INVENTION

It has been discovered that psychostimulants, e.g., cognition activators, can be administered via the transdermal preparations which contain one or more of 3-phenoxypyridine and its salts. Thus, compositions adapted for transmembrane absorption can be prepared and effectively administered, permitting treatment of such psychological disorders as memory loss, amnesia, senility, disorientation and the like.

DESCRIPTION OF THE INVENTION 3-phenoxypyridine is a known compound. The preparation, structure, and use of the compound and related derivatives, e.g., salts, have been disclosed in U.S. Pat. Nos. 4,067,983; 4,129,555; and 4,434,169, all of which are incorporated herein by reference. 3-phenoxypyridine base and certain pharmaceutically acceptable salts thereof are discussed in the literature. See Renshaw and Conn, *J. Am. Chem. Soc.* 59, 197 (1937), Butler, et al., *J. Med. Chem.*; 24,346 (1981). One pharmaceutically acceptable salt is the subject matter of U.S. Pat. No. 4,128,555. The use of 3-phenoxypyridine and its pharmaceutically acceptable salts for psychostimulation is reported in U.S. Pat. No. 4,067,983.

The structure of the base compound is shown in formula I:

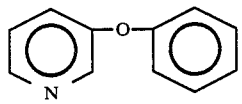
(I)

While the base, i.e., the compound of formula I, is a psychostimulant, its addition salts are too. Thus, compounds of formula II have similar biological activities to those of compounds of formula I:

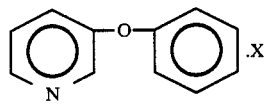
(II)

wherein X is a moiety which remains after the ionic interaction of the compound and of formula I or its functional equivalent(s) with an acidic reagent or other suitable reagent. The subject formulations may contain mixtures of compounds falling under both formulas, as well as combinations of two or more compounds of formula II.

Useful diluents include $C_{1-20}$ mono-alcohols, $C_{1-200}$ polyols, $C_{1-50}$ organic esters, water and mixtures thereof. Other useful diluents include buffers and the like. Preferred diluents include (e.g., buffers, triacetin, diacetin, monoacetin, propylene glycol, triethyl citrate, water, and the like. Mixtures are operable.

In order to enhance the stability of the salts in various diluent(s), the use of one or more optional buffering agents is contemplated. Useful buffers are those which control the pH of the buffered solution/dispersion to a value of about 5 to about 8, preferably about 5 to about 7. A pH of about 6 to about 10, preferably about 7.5 is preferred for the mono-sulfate salts of 3 phenoxypyridine. When buffer is present, the weight ratio of active ingredient—i.e., base or salt—to buffer in the diluent will be about 0.002:99.998 to about 0.14:99.86 (saturated solution solubility pH 7.0).

Useful buffering agents include conventional buffers, eg., phosphates and the like. Phosphate buffers are preferred. Mixtures of phosphates and other buffers are operable.

The transdermal formulations of the invention may contain, in addition to the active ingredients and other materials discussed above, one or more excipients. Generally, those pharmaceutical excipients are contemplated which do not significantly interfere with the function of the active ingredients, and any diluent(s) or buffer(s) used therewith. Useful excipients include one or more colorants, perfumes, surfactants, penetration enhancers, stabilizers, fillers and the like. Mixtures of excipients can be used.

Since the formulations are to be administered transdermally, the use of certain ingredients/substrates commonly found in compositions or devices to be applied to bodily membranes is preferred. Thus, components such as polymeric membranes (e.g., latexes) are useful herein.

The use of other therapeutic ingredients in the subject formulations is contemplated. Thus, suitable amounts of active ingredients whose functions are not deleterious to the operation of the active ingredients discussed above can be used.

The compositions of the invention are useful in the preparation of various devices by which therapeutic agents can be administered to animals via transmembranal delivery. Useful delivery devices include patches, films, sprays, swabs, suppositories, creams, gels, and the like with or without supportive backing materials.

While the compositions have been shown to be useful as human skin and mouse skin, it is contemplated that they be percutaneously administered to a wide variety of animals and not just to mammals. Transdermal, buccal, ocular, aural and vaginal administration are among the routes contemplated.

The dosage levels to be used in administering the instant formulations are generally consistent with those disclosed in U.S. Pat. No. 4,434,169.

The effectiveness of the preparations of the invention for the transdermal delivery of the subject compounds is demonstrated by the following examples:

EXAMPLE

Performance of Transdermal Formulations

The effectiveness of the subject base and a salt thereof when transdermally administered is set out in Table I.

TABLE I

Flux values of 3-phenoxypyridine and solutions of sulfate salt.

| Preparation | Flux (mcg/cm$^2$/h*) |
| --- | --- |
| 3-phenoxypyridine (neat) | 400 |
| 3-phenoxypyridine monosulfate in 0.2 molar phosphate buffer, pH 7.0 (wt. ratio of sulfate to buffer 0.14:99.86)** | 250 |
| 3-phenoxypyridine:propylene glycol:triacetin (wt. ratio, resp. 20:30:50) | >100 |
| 3-phenoxypyridine:propylene glycol:triethylcitrate (wt. ratio, resp. 20:30:50) | >100 |

*Flux values are expressed as weight ratio of ug 3-phenoxypyridine or monosulfate/cm$^2$/h. They were derived using a well known standard technique in which the cumulative amount of drug absorbed by the skin is plotted against time.
**Based on saturated solubility, 1.4 mg/ml = 0.14%.

Reasonable variations, such as those which would occur to a skilled artisan, can be made herein without departing from the scope of the invention.

We claim:

1. A transdermal psychostimulant composition containing a. an effective amount of a compound selected from the group consisting of 3-phenoxypyridine and an acid addition salt thereof, and b. an amount of one or more excipients which renders the composition administrable transmembranally and at least one diluent selected from the group consisting of propylene glycol, triacetin and triethylcitrate.

2. The composition of claim 1 wherein a phosphate buffer is also employed.

3. A patch containing the composition of claim 1.

4. A cream containing the composition of claim 1.

5. A gel containing the composition of claim 1.

6. A suppository containing the composition of claim 1.

7. A method of treating psychological disorders comprising administering to a subject via a body membrane, a composition which contains at least one compound selected from the group consisting of 3-phenoxypyridine and its acid addition salts.

8. The method of claim 1 comprising transdermal administration.

* * * * *